US012635925B2

(12) United States Patent
Nduka et al.

(10) Patent No.: US 12,635,925 B2
(45) Date of Patent: May 26, 2026

(54) METHOD AND APPARATUS FOR MEASURING BIOLOGICAL ELECTRICAL ACTIVITY

(71) Applicant: Emteq Limited, Falmer Brighton (GB)

(72) Inventors: Charles Nduka, Falmer Brighton (GB); Andrew Cleal, Falmer Brighton (GB); Mohsen Fatoorechi, Falmer Brighton (GB)

(73) Assignee: EMTEQ LIMITED, Brighton (GB)

( * ) Notice: Subject to any disclaimer, the term of this patent is extended or adjusted under 35 U.S.C. 154(b) by 1101 days.

(21) Appl. No.: 17/600,875

(22) PCT Filed: Apr. 2, 2020

(86) PCT No.: PCT/GB2020/050884
§ 371 (c)(1),
(2) Date: Oct. 1, 2021

(87) PCT Pub. No.: WO2020/201761
PCT Pub. Date: Oct. 8, 2020

(65) Prior Publication Data
US 2022/0167900 A1     Jun. 2, 2022

(30) Foreign Application Priority Data

Apr. 2, 2019     (GB) ..................................... 1904648

(51) Int. Cl.
*A61B 5/291*          (2021.01)
*A61B 5/00*           (2006.01)
(Continued)

(52) U.S. Cl.
CPC ................ *A61B 5/291* (2021.01); *A61B 5/24* (2021.01); *A61B 5/296* (2021.01); *A61B 5/6803* (2013.01);
(Continued)

(58) Field of Classification Search
None
See application file for complete search history.

(56) References Cited

U.S. PATENT DOCUMENTS

2009/0259137 A1* 10/2009 Delic ................... A61B 5/6843
600/545
2014/0247058 A1     9/2014 Mortara
(Continued)

FOREIGN PATENT DOCUMENTS

JP        2018-503481 A     2/2018
WO     WO2009/065006 A2     5/2009
(Continued)

OTHER PUBLICATIONS

International Search Report and Written Opinion for PCT Patent App. No. PCT/GB2020/050884 (Jun. 26, 2020).
(Continued)

*Primary Examiner* — Michael R Bloch
(74) *Attorney, Agent, or Firm* — KENEALY VAIDYA LLP

(57) ABSTRACT

Some embodiments are directed to an apparatus for measuring biological electrical activity, comprising: a plurality of sensors adapted for contact with a human or animal body; a signal injector configured to inject a reference signal into the body, the reference signal having a frequency substantially different to frequencies characteristic of the biological electrical activity; a lift-detection unit configured to receive signals from the plurality of sensors and, in dependence on the magnitude of the reference signal detected by each sensor, form a measure of the degree of contact between each respective sensor and the body; and a noise calculation unit configured to form an active cancellation signal by combining the signals detected by the sensors in dependence on their respective measures of the degree of contact with (Continued)

400

Inject out-of-band lift-detect signal into body — 402

Receive signals from sensors — 404

Form measure of contact between each sensor and the body in dependence on the magnitude of the lift-detect signal — 406

Weight signals from each sensor by degree of contact — 408

Filter out the lift-detect signal from received signals — 409

Determine active cancellation signal by taking weighted average of received signals — 410

Inject active cancellation signal into body — 412 the body and to cause the signal injector to inject the active cancellation signal into the body.

15 Claims, 3 Drawing Sheets

(51) Int. Cl.
    *A61B 5/24*         (2021.01)
    *A61B 5/296*      (2021.01)

(52) U.S. Cl.
    CPC .......... *A61B 5/6814* (2013.01); *A61B 5/6843* (2013.01); *A61B 5/6844* (2013.01); *A61B 5/7203* (2013.01); *A61B 5/721* (2013.01); *A61B 5/725* (2013.01); *A61B 2562/0219* (2013.01)

(56)              References Cited

U.S. PATENT DOCUMENTS

| | | | |
|---|---|---|---|
| 2015/0157255 A1* | 6/2015 | Nduka | A61B 5/389 |
| | | | 600/587 |
| 2017/0135640 A1 | 5/2017 | Gunasekar et al. | |
| 2018/0317848 A1* | 11/2018 | Gunasekar | A61B 5/6843 |

FOREIGN PATENT DOCUMENTS

| | | |
|---|---|---|
| WO | WO2009/087486 A2 | 7/2009 |
| WO | WO2016/094014 A1 | 6/2016 |

OTHER PUBLICATIONS

Search Report from British Patent App. No. GB1904648.1 (Dec. 11, 2019).

* cited by examiner

METHOD AND APPARATUS FOR MEASURING BIOLOGICAL ELECTRICAL ACTIVITY

CROSS REFERENCE TO RELATED APPLICATIONS

This application is a national phase filing under 35 C.F.R. § 371 of and claims priority to PCT Patent Application No. PCT/GB2020/050884, filed on Apr. 2, 2020, which claims the priority benefit under 35 U.S.C. § 119 of British Patent Application No. 1904648.1, filed on Apr. 2, 2019, the contents of each of which are hereby incorporated in their entireties by reference.

BACKGROUND

Some embodiments of the presently disclosed subject matter relate to apparatus and methods for measuring biological electrical activity.

Traditionally, biological electrical activity sensors have been fixed to the body. For example, surface electromyography (EMG) recording sensors or electrocardiography (ECG) electrodes are commonly held against the body with adhesive tape or a self-adhesive sticker/pad.

As the quality of the signals obtained by such sensors is strongly dependent on the contact between the sensor and the body, care is taken to prepare the surface of the body to ensure a sound contact by removing hair and cleaning the surface with alcohol.

However, the use of such sensors is wholly unsuitable for certain applications. For example, on the face, or parts of the body which frequently move or where the skin frequently wrinkles and stretches can render the adhesives holding the sensors ineffective, and some users can develop allergies to the adhesives used. Furthermore, the onerous application process described above can render the sensors unsuitable for casual use, or use in the home by non-medical consumers.

To overcome some of these issues, systems using non-adhesive sensors have been developed in recent years. These systems, however, have encountered further problems related to sensors lifting from the surface of the body and artefacts in the signal caused by movement of the body, each of which degrades the quality of the measured signals and can lead to the capture of erroneous data.

All of the systems above encounter interference in their measured signals due to ambient electric- and magnetic-fields, major sources of which include the mains electric power system and nearby radio, television or radar facilities. Such sources can couple to the body or the measurement device capacitively or via magnetic induction. Though such noise can be unpredictable, it is generally picked up uniformly across the body and the electrodes and hence it is referred to as "common-mode" noise or interference.

A partial solution to the problem of common-mode noise is shown in the known circuit 100 of FIG. 1, known as a "driven right leg" (DRL) circuit. A patient 102 has their arms connected to two ECG electrodes 104 and 106. The common-mode voltage of the body is derived from the signal common to the signals from the electrodes 104 and 106—for example, by averaging the signals from the electrodes 104 and 106 using the resistor and amplifier network shown in FIG. 1. This common-mode voltage is then inverted and amplified by op-amp 112 and fed back to the right leg. On the basis that the component common to well-spaced electrodes 104 and 106 substantially includes noise, this provides a negative feedback loop that cancels environmental noise at the sensors and drives the common-mode voltage to a low value.

SUMMARY

According to some embodiments of the presently disclosed subject matter there is provided an apparatus for measuring biological electrical activity, including: a plurality of sensors adapted for contact with a human or animal body; a signal injector configured to inject a reference signal into the body, the reference signal having a frequency substantially different to frequencies characteristic of the biological electrical activity; a lift-detection unit configured to receive signals from the plurality of sensors and, in dependence on the magnitude of the reference signal detected by each sensor, form a measure of the degree of contact between each respective sensor and the body; and a noise calculation unit configured to form an active cancellation signal by combining the signals detected by the sensors in dependence on their respective measures of the degree of contact with the body and to cause the signal injector to inject the active cancellation signal into the body.

The noise calculation unit may be configured to form the active cancellation signal by forming a weighted average of the signals detected by the sensors, wherein the signal detected by each sensor is weighted according to the measure of the degree of contact between that sensor and the body.

The noise calculation unit may be configured to down-weight signals detected by sensors with lower measures of the degree of contact relative to signals detected by sensors with higher measures of the degree of contact.

The noise calculation unit may be configured to down-weight signals detected by sensors whose respective measures of the degree of contact are below a predefined threshold.

The noise calculation unit may be configured to down-weight signals detected by sensors in proportion to their measure of the degree of contact of the sensors relative to the predefined threshold, with signals detected by sensors further below the predefined threshold being downweighted to a greater degree than signals detected by sensors closer to the predefined threshold.

The measure of the degree of contact may be a binary measure indicating whether a sensor is or is not in contact with the body in dependence on whether the magnitude of the reference signal detected by that sensor is above or below a predetermined threshold, respectively.

The noise calculation unit may be configured to only combine the signals detected by sensors whose measure of the degree of contact indicate that those sensors are in contact with the body.

The apparatus may further include inertial motion units associated with one or more of the sensors, configured to form a measure of the movement of the respective one or more of the sensors, and wherein the noise calculation unit is configured to combine the signals detected by the one or more sensors in dependence on the measure of movement formed by the inertial motion unit associated with the one or more sensors.

The noise calculation unit may be configured to remove the reference signal from the signals detected by the plurality of sensors prior to combining those signals so as to form the active cancellation signal.

The noise calculation unit may further include a filter configured to remove the reference signal from the signals detected by the plurality of sensors.

The filter may be a band-stop or low-pass filter configured to attenuate frequencies at the reference signal frequency but pass frequencies below the reference signal.

The sensors may be configured to detect electromyographic signals.

The lift-detection unit may be further configured to identify patterns in the signals detected by the sensors characteristic of one or more facial expressions.

There is also provided headwear including the apparatus as described above. There is also provided glasses including the apparatus as described above. The signal injector may be located on an arm of the glasses such that it contacts the skin behind the ear of a wearer.

There is also provided a method for measuring biological electrical activity using a plurality of sensors adapted for contact with a human or animal body, the method including: injecting a reference signal into the body, the reference signal having a frequency substantially different to frequencies characteristic of the biological electrical activity; receiving signals detected by the plurality of sensors; forming a measure of the degree of contact between each sensor and the body in dependence on the magnitude of the reference signal detected by each sensor; forming an active cancellation signal by combining the signals detected by the sensors in dependence on their respective measures of the degree of contact with the body; and injecting the active cancellation signal into the body.

The forming of the active cancellation signal may include forming a weighted average of the signals detected by the sensors, wherein the signal detected by each sensor is weighted according to the measure of the degree of contact between that sensor and the body.

Signals detected by sensors with lower measures of the degree of contact may be downweighted relative to signals detected by sensors with higher measures of the degree of contact.

The signals detected by sensors whose respective measures of the degree of contact are below a predefined threshold may be downweighted.

The frequency of the reference signal may be substantially above the frequencies characteristic of the biological electrical activity. The frequency of the reference signal may be greater than 500 Hz. The frequency of the reference signal may be greater than 1000 Hz. The frequency of the reference signal may be between 1000 Hz and 2000 Hz. The frequency of the reference signal may be between 1250 Hz and 1750 Hz.

The frequencies characteristic of the biological electrical activity may be between 20 and 450 Hz.

DESCRIPTION OF THE DRAWINGS

Some embodiments of the presently disclosed subject matter will now be described by way of example with reference to the accompanying drawings. In the drawings.

DETAILED DESCRIPTION OF EXEMPLARY EMBODIMENTS

The following description is presented to enable any person of ordinary skill in the art to make and use of some embodiments of the present the invention and is provided in the context of a particular application. Various modifications to the disclosed embodiments will be readily apparent to those of ordinary skill in the art.

The general principles defined herein may be applied to other embodiments and applications without departing from the spirit and scope of the presently disclosed subject matter. Thus, some embodiments of the presently disclosed subject matter are not intended to be limited to the embodiments shown but is to be accorded the widest scope consistent with the principles and features disclosed herein.

Figure 1:
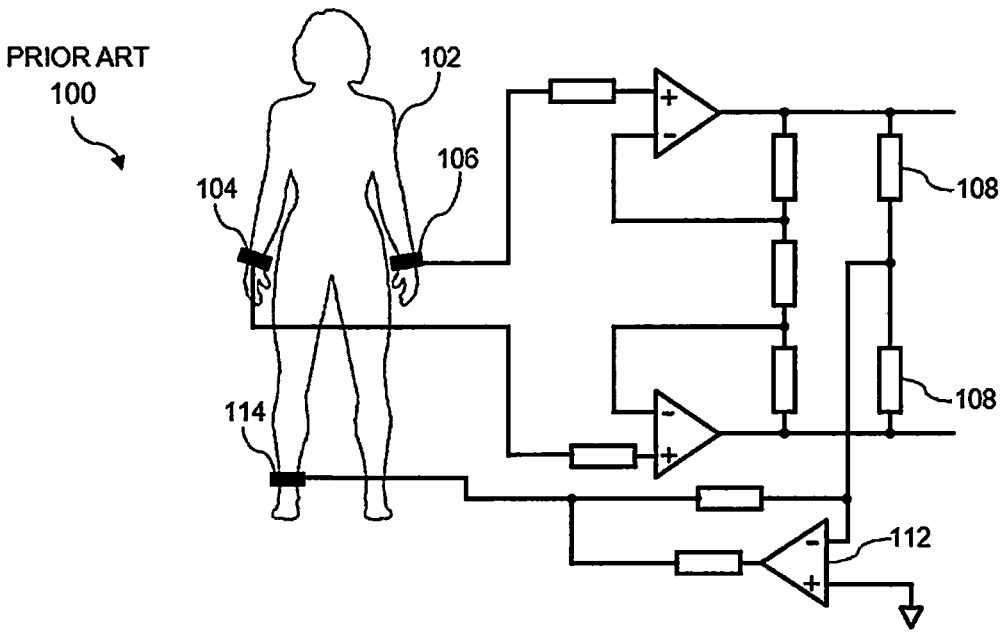
FIG. 1 shows a schematic diagram of a known DRL circuit.

The system shown in FIG. 1 can suffer from problems when one of the electrodes 104 or 106 detaches or makes a poor connection to the body. This can result in one of the electrodes 104 or 106 not benefitting from the cancellation of the DRL circuit (since that electrode does not receive the common-mode cancellation signal), whilst that electrode still contributes to the common-mode voltage. This has the effect of degrading the quality of the signal from the electrode which is still in contact with the body. In some cases, the noise received at the fully or partially detached sensor will increase, leading to a net injection of noise into the system rather than a cancellation of common-mode noise at the sensors.

The present disclosure addresses these problems.

Figure 2:
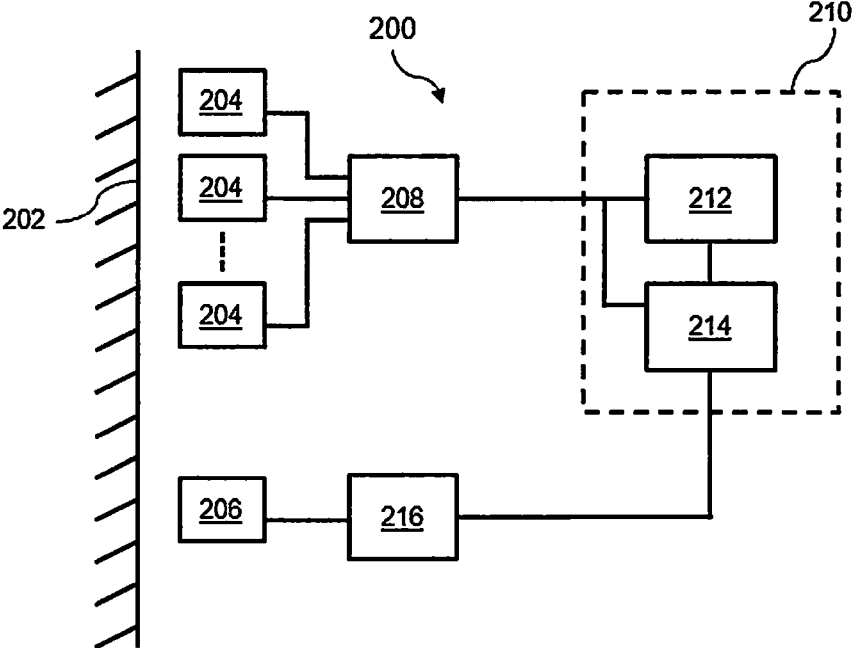
FIG. 2 shows a schematic diagram of a device capable of an apparatus capable of measuring biological electrical activity.

FIG. 2 illustrates an exemplary apparatus 200 including a plurality of biological electrical activity sensors 204. The sensors may be configured to detect one or more of EEG (electroencephalogram), ECG (electrocardiogram), EOG (electrooculography) and EMG (electromyogram) signals from the body 202 of a person or animal. Each type of biological electrical activity will generally lie within a characteristic frequency range. For example, frequencies within the range of 20 to 450 Hz are typically characteristic of electrical muscle activity.

Suitable sensor types include surface electromyographic (sEMG) sensors (e.g. contact sensors, such as those manufactured by mc10 or Toumaz) and electric potential (EP) sensors (e.g. such as Plessey EPIC sensors). It can be advantageous to use electric potential sensors because these exhibit high sensitivity and do not require a conductive medium such as a gel or conductive adhesive patch to electrically couple the sensor to the skin.

A signal injector 206 is configured to inject an electrical reference signal, into the body 202. The signal injector 206 may be, for example, one or more electrodes. The signal injector 206 may inject signals into the body 202 at a single location, or at a plurality of different locations. A lift-detect signal is an example of a reference signal. The signal injector 206 may be configured to inject a lift-detect signal at a single frequency or a plurality of different frequencies.

The sensors 204 are configured such that they can detect signals across a frequency range that encompasses the frequencies of the biological electrical and the lift-detect signal. The lift-detect signal has a substantially different frequency to that of the biological electrical activity that is to be measured. Preferably or advantageously, the frequency of the lift-detect signal should be sufficiently different from that of the biological electrical activity that is to be measured, so these signals can be easily separated. For example, for electrical muscle activity, which is typically within the range of 20 to 450 Hz, a lift-detect signal of greater than 1 kHz may be used. The lift-detect signal may be a greater frequency than that of the biological electrical activity being measured. The lift-detect signal may have a frequency that is 1.1, 1.5, 2, 5, 10 or 100 times greater than the frequencies characteristic of the biological electrical activity being measured. The lift-detect signal may have a frequency of at least 1 kHz. The lift-detect signal may have a frequency in the range of 1000 to 2000 Hz, or 1250 Hz to 1750 Hz. The maximum practical frequency of the lift-detect signal is determined by the capabilities of the electronics described below and the electrical characteristics of the human or animal body.

Each sensor 204 may be connected to an analogue-to-digital converter (ADC) 208 that converts the electrical signals detected by the sensors 204 to a digital signal, suitable to be processed by digital electronics. ADC 208 may then pass the converted signals to a lift-detection unit 212. The lift-detection unit 212 is configured to determine the magnitude of the lift-detect signal received at each of the sensors—for example, the lift-detection unit 212 may be configured to determine the magnitude of the signals received by each of the sensors 204 at the frequency of the lift-detect signal. The magnitude of a signal may be any suitable measure of the strength of a signal, such as one or more of: amplitude, energy or power content over a pre-defined range of frequencies, a measure of the average or maximum signal at a predefined frequency or over a pre-defined range of frequencies. The lift-detection unit 212 may be configured to determine the amplitudes of the signals received by each of the sensors 204.

Any suitable technique may be used to determine the magnitude of the lift-detect signals received at each sensor. For example, a filter (such as a band-pass filter configured to pass the frequency of the lift-detect signal) may be used to isolate the lift-detect signal from each sensor and its magnitude determined by measuring the energy or power of that isolated signal. For example, a Fourier analysis (e.g. using a fast Fourier transform or FFT) could be used to identify the energy of the frequency components at the frequency of the lift-detect signal. In some implementations a phase-locked loop could be used to extract the lift-detect signal received at each sensor.

The lift-detection unit 212 is configured to form a measure of the degree of contact between each sensor 204 and the body 202. This measure is formed in dependence on the magnitude of the lift-detect signal received by each sensor 204. The degree of contact between a sensor 204 and the body may vary in dependence on several factors. Examples of these factors include: the relative orientation of the sensor and the body, the force with which a sensor is pressed against the body, and the presence of moisture, hair and other skin contaminants between the sensor and the body.

The measure of the degree of contact may be a binary indication, e.g. an indication of either contact or no contact. The binary indication may be determined depending on whether or not the magnitude of the lift-detect signal received by a given sensor 204 is above or below a predetermined threshold. For example, sensors 204 which receive the lift-detect with a magnitude above the predetermined threshold may be determined to be in contact with the body 202. Conversely, sensors 204 which receive the lift-detect with a magnitude below the predetermined threshold may be determined to not be in contact with the body 202.

A suitable predetermined threshold may be established in any suitable manner—e.g. empirically and/or through a calibration process. The predetermined threshold may be a static value or the lift-detection unit 212 may be configured to vary the threshold during operation. The predetermined threshold may be set during a calibration process such that, in a given signal environment, the threshold for a sensor 204 is set in dependence on the magnitude of the lift-detect signal at the point a sensor 204 is deemed to lose contact with the body 202 (e.g. when the sensor loses physical contact with the body or when the sensor is some predefined distance from the body).

In some implementations, the threshold may be set for a sensor in dependence on the level of the lift-detect signal relative to the noise level in the signal according to any suitable measure of signal noise—for example, the threshold may be set at the point at which the ratio of the magnitude of the lift-detect signal to the magnitude of the signal noise is some predefined ratio. For example, the predefined ratio may include the magnitude of the lift-detect signal being 10, 5, 2 or 1 times greater than the magnitude of the signal noise. In general, a sensor 204 that loses contact with the body can no longer provide useful data for a given application. Each sensor may have its threshold independently set, one or more groups of sensors may have their threshold set together, or all or most of the sensors may have a common threshold set for them. Sensors may have their thresholds set differently as the strength of the coupling between each sensor and the signal injector 206 can vary depending on their relative location. For example, the threshold for a given sensor may vary in dependence on its distance from the signal injector 206. Sensors further away from the signal injector may have a lower threshold than sensors nearer to the signal injector 206. In some examples, different sensors may be different types of sensors and so may have different thresholds.

The measure of contact may be a continuous measure which varies in dependence on the magnitude of the lift-detect signal. For example, the measure may decrease from a maximum value (when the sensor 204 is in firm contact with the body 202) as the contact becomes poorer until the measure reaches a minimum when no lift-detect signal is detected.

The system 200 further includes a noise calculation unit 214. The noise calculation unit 214 is configured to form an active cancellation signal by combining signals received by the sensors 204. The noise calculation unit 214 is configured to combine the signals received by the sensors 204 in dependence on the measure of the degree of contact of the sensors 204 with the body 202. The noise calculation unit 214 is configured to cause the signal injector 206 to provide the active cancellation signal to the body. The noise calculation unit 214 may operate in a similar manner to the DRL system described in relation to FIG. 1, wherein a common-mode voltage on the body is derived—for example, by averaging the received signals, inverting the average, and feeding it back to the body. In accordance with the principles described herein the input of the sensors 204 may be weighted according to their degree of contact with the body 202, as is described in more detail below.

In general, any suitable technique may be used for combining the signals from the sensors so as to capture the noise signal common to the set of sensors 204 for use as the active cancellation signal. More complex approaches can be used than simply averaging the signals received from the sensors—for example, statistical or Fourier analyses may be used as is known in the art of signal processing. It can be necessary to scale the signals received from sensors so as to account for variations in sensitivity between sensors.

The lift-detect signal itself is preferably or advantageously filtered out and/or cancelled from the signals received from the sensors prior to combining the sensor signals so as to form the active cancellation signal. This may be achieved, for example, through the use of a band-stop filter configured to attenuate signals at the frequency of the lift-detect signal, and/or by a low-pass filter configured to attenuate signals at or above the frequency of the lift-detect signal (e.g. in examples in which the characteristic frequencies of the biological signals are below the lift-detect signal), and/or by combining each received signal with an inverted and optionally scaled copy of the lift-detect signal so as to cancel the lift-detect signals present the signals from the sensors.

The noise calculation unit 214 may form its active cancellation signal in any suitable manner, including in the analogue or digital domain. In FIG. 2, the noise calculation unit 214 is shown as operating in the digital domain. The system may further include a digital-to-analogue converter (DAC) 216 configured to convert a digital active cancellation signal into an analogue signal. Prior to causing the signal injector 206 to provide the active cancellation signal to the body, the noise calculation unit 214 may use any suitable noise filter to filter out the contribution of the lift-detect signal to the active cancellation signal. For example, a filter such as a band-pass filter configured to filter out the frequency of the lift-detect signal may be used.

The lift-detection unit 212 and the noise calculation unit 214 may be implemented into the same device, as shown in FIG. 2, referred to as the control device 210. The lift-detection unit 212, noise calculation unit 214 and control device 210.

Sensors 204 in poor contact with the body 202 will generally benefit less from the active noise cancellation by virtue of their poor contact with the body. These sensors 204 will therefore have a low signal-to-noise ratio. Thus, the feedback loop of active noise cancellation which drives the noise to a low level during ideal operation can be disrupted. This can result in the active cancellation signal being a poor representation of the real unwanted noise, resulting in a degradation of the signal-to-noise ratio in the signals received by all or most sensors. Furthermore, in some situations, sensors in poor contact with the body may receive greater environmental noise than sensors in good contact with the body. Hence, forming an active cancellation signal by combining the signals received by sensors in dependence on measures of the degree of contact provides an improved active cancellation signal when compared with known DRL systems.

The noise calculation unit 214 may form the active cancellation signal by calculating a weighted average of the received signals. The individual signals from respective sensors 204 may be weighted according to the degree of contact between each respective sensor 204 and the body 202. The signals from sensors 204 with a low degree of contact may be completely disregarded (equivalent to downweighting the signals from those sensors to zero). The signals from sensors 204 that have been disregarded (or downweighted to zero) will therefore not contribute to the determination of the active cancellation signal.

The functions of the lift-detection unit 212 and noise calculation unit 214 may be performed by the same device, i.e. a control device 210, as shown in FIG. 2. These units/devices may be implemented using one or more of: algorithms programmed into firmware, hardware and software.

Figure 3:
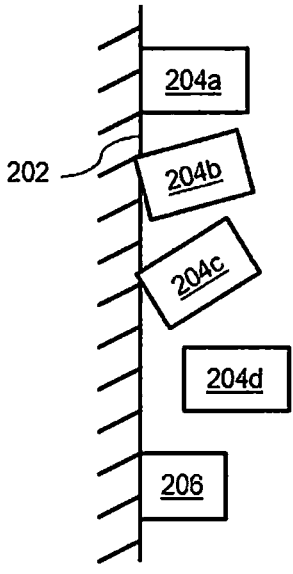
FIG. 3 shows an exemplary arrangement of a noise calculation unit and sensors for measuring biological electrical activity exhibiting a range of degrees of contact.

FIG. 3 shows an example including four sensors 204a, 204b, 204b and 204d in varying degrees of contact with the body 202. Signal injector 206 is shown injecting the lift-detect signal and the active cancellation signal and should preferably or advantageously be maintained in good contact with the body 202. Sensor 204a is also in good contact with the body 202, receiving the active cancellation signal at an ideal magnitude and the lift-detect signal at a large magnitude.

Sensor 204b is shown with a lesser/worse degree of contact. Thus, sensor 204b may not fully benefit from the active cancellation signal and may only receive the lift-detect signal with an intermediate magnitude. If the measure of the degree of contact between sensor 204b and the body 202 is binary, the signal from the sensor 204b may or may not be excluded from contributing to the determination of the active cancellation signal, depending on the predetermined threshold. If the measure of the degree of contact between sensor 204b and the body 202 is continuous, the signal from the sensor 204b may be downweighted in the determination of the active cancellation signal.

Sensor 204c is shown with a particularly bad degree of contact. Thus, sensor 204c may hardly benefit from the active cancellation signal and may only receive the lift-detect signal with a negligible magnitude. If the measure of the degree of contact between sensor 204c and the body 202 is binary, the signal from the sensor 204c will be excluded from contributing to the determination of the active cancellation signal. If the measure of the degree of contact between sensor 204c and the body 202 is continuous, the signal from the sensor 204c may be downweighted in the determination of the active cancellation signal. The signal from sensor 204c may be downweighted to zero.

Sensor 204d is not in contact with the body. Thus, sensor 204d will not benefit from the active cancellation signal and will not receive the lift-detect signal. As with sensor 204c, if the measure of the degree of contact between sensor 204d and the body 202 is binary, the signal from the sensor 204d will be excluded from contributing to the determination of the active cancellation signal. If the measure of the degree of contact between sensor 204d and the body 202 is continuous, the signal from the sensor 204d may be heavily downweighted in the determination of the active cancellation signal. The signal from sensor 204d may be downweighted to zero.

Figure 4:
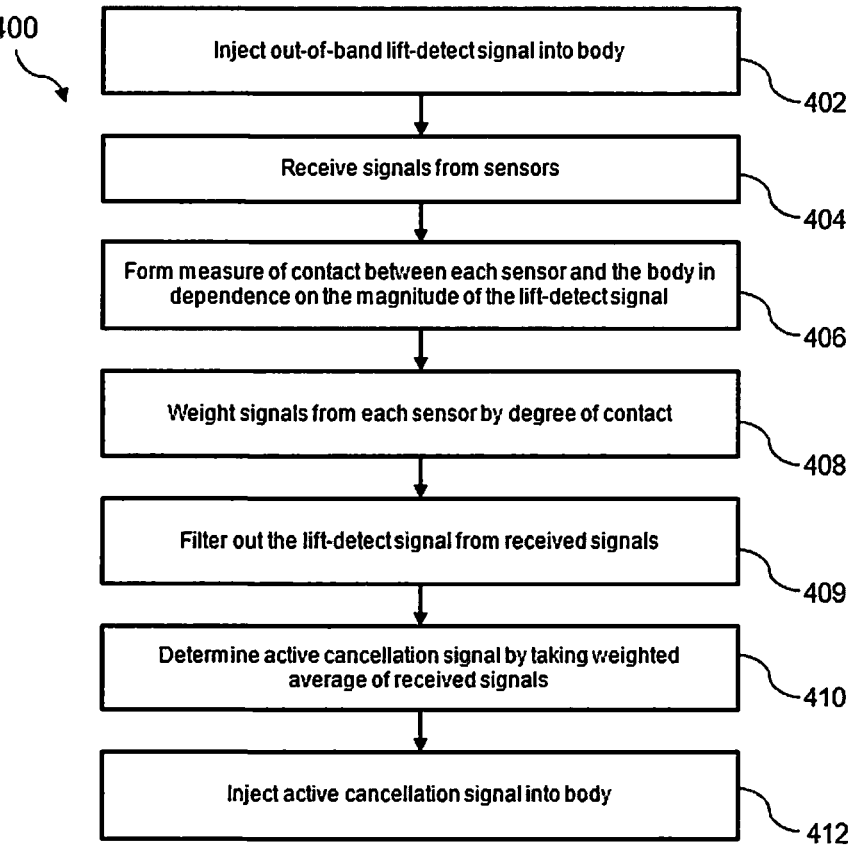
FIG. 4 shows a flowchart illustrating a process for measuring biological electrical activity.

A method 400 by which lift is detected and used to improve noise cancellation is shown in FIG. 4. In the first step 402, an out-of-band lift-detect signal is injected into the body. In the second step 404, signals are received from each of the sensors. As described above, the signals will generally contain, to some degree, the desired biological signal, the lift-detect signal, and common-mode noise. In the third step 406, a measure of contact between each sensor and the body is formed in dependence on the magnitude of the lift-detect. In the fourth step 408, the signals from each sensor are weighted according to the measure of the degree of contact with the body. As discussed above, sensors in poor contact with the body will have their contributions reduced. In the fifth step 409, the lift-detect signal is filtered out of the received signals. In the sixth step 410, an active cancellation signal is determined by taking a weighted average of the signals, using the weights from step 408. The active cancellation signal is then injected into the body in the seventh step 412, by way of an electrode in contact with the body.

Applications of some embodiments of the presently disclosed subject matter include any system in which the contact between biological electrical sensors and a body cannot be assured. Any use of these sensors which does not use gels and adhesives, such as personal users in a non-clinical setting can benefit from the present invention. One such application of some embodiments of the presently disclosed subject matter is face monitoring headwear (and/or facewear). Sensors intended for contact with the face often suffer from a poor degree of contact with the skin due to the frequent, varied and unpredictable motion of the face. Facial movements may result from facial expressions, talking, eating, twitches and tics. Due to these movements of the face, it is difficult to provide sensors on facewear which are held in good contact with the skin at all or most times. Furthermore, these facial movements make adhesive sensors unsuitable for use on the face. For these reasons, facewear mounted sensors can particularly benefit from compensation for the degree of contact provided by the presently disclosed subject matter. The apparatus 200 may be integrated into a pair of glasses. Glasses including the apparatus 200 are particularly suited for measuring biological electrical activity in an unobtrusive and inconspicuous manner. Glasses including the apparatus 200 allow the biological electrical activity to be measured without impeding a wearer's movement or vision.

Figure 5:
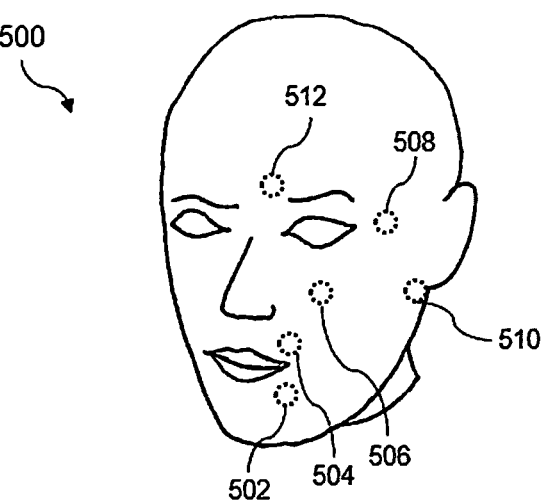
FIG. 5 shows exemplary locations for sensors suitable for identifying and monitoring facial expressions.

FIG. 5 shows an exemplary use 500 of the presently disclosed subject matter for accurately and reliably identifying and monitoring facial expressions. EMG sensors could be positioned at one or more of the identified locations 502 to 510, where they would be able to monitor the electrical activity of muscles underlying the skin. The contact between the sensors and the skin can be significantly affected by the bunching of skin during certain facial expressions. For example, the contact between a sensor at location 512 may be significantly different during a frown than when relaxed, due to the skin bunching.

Certain locations may be more suited to signal injectors as opposed to sensors. For example, behind the ear at location 510 is particularly suited for the injection of signals, as performed by signal injector 206, as components at this location do not obscure or obstruct the face. If the apparatus 200 is integrated into a pair of glasses, one or more electrodes of the signal injector 206 may be positioned on the arm of the glasses (e.g. at the distal end of the arm of the glasses) such that the signal injector 206 contacts the skin behind the ear.

Using some embodiments of the presently disclosed subject matter on and around the face can provide further benefits. For example, the measure of the degree of contact, as determined by the lift-detection unit 212 may be indicative of the facial expression of a user. More specifically, the lift-detection unit 212 may be configured to identify patterns in the signals from the sensors 204 characteristic of one or more facial expressions. The lift-detection unit 212 may determine a facial expression by identifying patterns in the biological electrical signals and lift-detect signals received by the sensors 204. This is advantageous as previous systems simply used the biological electrical systems and treated sensor lifting as an unwanted effect.

The apparatus 200 may further include one or more inertial motion units (not shown). Each inertial motion unit may be associated with one or more of the sensors 204 and be configured to form a measure of the movement of those one or more sensors. The movement of sensors may provide a further measure of the degree of contact between those sensors. Sensors experiencing movement may experience varying degrees of contact. The noise calculation unit may be configured to combine signals from sensors in dependence on the movement measured by the inertial motion unit associated with those sensors. The noise calculation unit may downweight signals from sensors with a measure of movement above a predefined threshold.

The applicant hereby discloses in isolation each individual feature described herein and any combination of two or more such features, to the extent that such features or combinations are capable of being carried out based on the present specification as a whole in the light of the common general knowledge of a person of ordinary skill in the art, irrespective of whether such features or combinations of features solve any problems disclosed herein, and without limitation to the scope of the claims. The applicant indicates that some embodiments of the presently disclosed subject matter can include or can consist of any such individual feature or combination of features. In view of the foregoing description it will be evident to a person of ordinary skill in the art that various modifications may be made within the scope of the invention.

The invention claimed is:

1. An apparatus for measuring biological electrical activity, the apparatus comprising:
   a plurality of sensors adapted for contact with a human or animal body and configured to detect signals from the human or animal body;
   a signal injector configured to inject a reference signal into the human or animal body, the reference signal having a frequency different to frequencies characteristic of the biological electrical activity;
   a lift-detection unit configured to receive signals from the plurality of sensors and, in dependence on a magnitude of the reference signal detected by each sensor, form a measure of a degree of contact between each respective sensor and the human or animal body; and
   a noise calculation unit configured to:
      form an active cancellation signal by combining the signals detected by the plurality of sensors so as to capture a noise signal common to the plurality of sensors, wherein the signals detected by the plurality of sensors are combined in dependence on their respective measures of the degree of contact with the human or animal body; and
      cause the signal injector to inject the active cancellation signal into the human or animal body so as to counteract the noise signal common to the plurality of sensors,
   wherein the noise calculation unit is configured to downweight signals detected by sensors of the plurality of sensors whose respective measures of the degree of contact are below a predefined threshold,
   wherein the noise calculation unit is configured to downweight signals detected by sensors of the plurality of sensors in proportion to their measure of the degree of contact relative to the predefined threshold, with signals detected by sensors of the plurality of sensors further below the predefined threshold being downweighted to a greater degree than signals detected by sensors of the plurality of sensors closer to the predefined threshold.

2. The apparatus as claimed in claim 1, wherein the noise calculation unit is configured to form the active cancellation signal by forming a weighted average of the signals detected by the plurality of sensors, wherein the signal detected by each sensor is weighted according to the measure of the degree of contact between that sensor and the human or animal body.

3. The apparatus as claimed in claim 2, wherein the noise calculation unit is configured to downweight signals detected by sensors of the plurality of sensors with lower measures of the degree of contact relative to signals detected by sensors of the plurality of sensors with higher measures of the degree of contact.

4. The apparatus as claimed in claim 1, further comprising inertial motion units associated with one or more sensors of the plurality of sensors, configured to form a measure of the movement of a respective sensor of the one or more sensors of the plurality of sensors, and wherein the noise calculation unit is configured to combine the signals detected by the one or more sensors in dependence on the measure of movement formed by the inertial motion unit associated with the one or more sensors.

5. The apparatus as claimed in claim 1, wherein the frequency of the reference signal is above the frequencies characteristic of the biological electrical activity.

6. The apparatus as claimed in claim 1, wherein the noise calculation unit is configured to remove the reference signal from the signals detected by the plurality of sensors prior to combining those signals so as to form the active cancellation signal.

7. The apparatus as claimed in claim 6, wherein the noise calculation unit includes a filter configured to remove the reference signal from the signals detected by the plurality of sensors.

8. The apparatus as claimed in claim 7, wherein the filter is a band-stop or low-pass filter configured to attenuate frequencies at the reference signal frequency but pass frequencies below the reference signal.

9. The apparatus as claimed in claim 1, wherein the plurality of sensors are configured to detect electromyographic signals.

10. The apparatus as claimed in claim 1, wherein the lift-detection unit is further configured to identify patterns in the signals detected by the plurality of sensors characteristic of one or more facial expressions.

11. A headwear comprising the apparatus as claimed in claim 1.

12. A pair of glasses comprising the apparatus as claimed in claim 1, wherein the signal injector is located on an arm of the glasses such that it is adapted to contact skin behind an ear on the human or animal body.

13. A method for measuring biological electrical activity using a plurality of sensors adapted for contact with a human or animal body and configured to detect signals from the human or animal body, the method comprising:

injecting a reference signal into the human or animal body, the reference signal having a frequency different to frequencies characteristic of the biological electrical activity;

receiving signals detected by the plurality of sensors;

forming a measure of a degree of contact between each sensor and the human or animal body in dependence on a magnitude of the reference signal detected by each sensor;

forming an active cancellation signal by combining the signals detected by the plurality of sensors so as to capture a noise signal common to the plurality of sensors, wherein the signals detected by the plurality of sensors are combined in dependence on their respective measures of the degree of contact with the human or animal body, wherein forming the active cancellation signal comprises downweighting signals detected by sensors of the plurality of sensors whose respective measures of the degree of contact are below a predefined threshold, wherein signals detected by sensors of the plurality of sensors are downweighted in proportion to their measure of the degree of contact relative to the predefined threshold, with signals detected by sensors of the plurality of sensors further below the predefined threshold being downweighted to a greater degree than signals detected by sensors of the plurality of sensors closer to the predefined threshold; and injecting the active cancellation signal into the human or animal body so as to counteract the noise signal common to the plurality of sensors.

14. The method as claimed in claim 13, wherein the forming of the active cancellation signal comprises forming a weighted average of the signals detected by the plurality of sensors, wherein the signal detected by each sensor is weighted according to the measure of the degree of contact between that sensor and the human or animal body.

15. The method as claimed in claim 14, wherein signals detected by sensors of the plurality of sensors with lower measures of the degree of contact are downweighted relative to signals detected by sensors of the plurality of sensors with higher measures of the degree of contact.

* * * * *